United States Patent
Mittal et al.

(10) Patent No.: US 11,077,050 B2
(45) Date of Patent: Aug. 3, 2021

(54) FORMULATION FOR PARENTERAL ADMINISTRATION

(71) Applicants: MERCK SHARP & DOHME CORP., Rahway, NJ (US); MERCK SHARP & DOHME B. V., Haarlem (NL); Sachin Mittal, Bridgewater, NJ (US); Irina Kazakevich, Rockaway, NJ (US); Himanshu Bhattacharjee, Princeton, NJ (US); Peter Bakker, Zeist (NL); Luke Schenck, Yardley, PA (US); David J. Goldfarb, Highland Park, NJ (US); Amitava Mitra, Princeton, NJ (US); Donna Carroll, Garwood, NJ (US); Nazia Khawaja, Morris Plains, NJ (US)

(72) Inventors: Sachin Mittal, Bridgewater, NJ (US); Irina Kazakevich, Rockaway, NJ (US); Himanshu Bhattacharjee, Princeton, NJ (US); Peter Bakker, Zeist (NL); Luke Schenck, Yardley, PA (US); David J. Goldfarb, Highland Park, NJ (US); Amitava Mitra, Princeton, NJ (US); Donna Carroll, Garwood, NJ (US); Nazia Khawaja, Morris Plains, NJ (US)

(73) Assignees: Merck Sharp & Dohme Corp., Rahway, NJ (US); Merck Sharp & Dohme B.V., Haarlem (NL)

( * ) Notice: Subject to any disclaimer, the term of this patent is extended or adjusted under 35 U.S.C. 154(b) by 131 days.

(21) Appl. No.: 16/496,182

(22) PCT Filed: Mar. 19, 2018

(86) PCT No.: PCT/US2018/023051
§ 371 (c)(1),
(2) Date: Sep. 20, 2019

(87) PCT Pub. No.: WO2018/175271
PCT Pub. Date: Sep. 27, 2018

(65) Prior Publication Data
US 2020/0289406 A1 Sep. 17, 2020

Related U.S. Application Data

(60) Provisional application No. 62/476,034, filed on Mar. 24, 2017.

(51) Int. Cl.
*A61K 31/4439* (2006.01)
*A61K 9/00* (2006.01)
*A61K 47/10* (2017.01)
*A61K 47/22* (2006.01)
*A61K 47/26* (2006.01)
*A61K 47/38* (2006.01)
*A61K 9/10* (2006.01)

(52) U.S. Cl.
CPC ........ *A61K 9/0019* (2013.01); *A61K 31/4439* (2013.01); *A61K 47/10* (2013.01); *A61K 47/22* (2013.01); *A61K 47/26* (2013.01); *A61K 47/38* (2013.01); *A61K 9/10* (2013.01); *C07B 2200/13* (2013.01)

(58) Field of Classification Search
CPC .......................... A61K 31/4439; A61K 9/0019
See application file for complete search history.

(56) References Cited

U.S. PATENT DOCUMENTS

| | | | |
|---|---|---|---|
| 6,143,778 A | 11/2000 | Gautier et al. | |
| 8,486,975 B2 | 7/2013 | Burch et al. | |
| 9,150,539 B2 | 10/2015 | Maguire | |
| 2013/0171214 A1 | 7/2013 | Mundhra et al. | |

OTHER PUBLICATIONS

Baert, L. et al., Development of a long-acting injectable formulation with nanoparticles of rilpivirine (TMC278) for HIV treatment, European Journal of Pharmaceutics and Biopharmaceutics, 2009, 502-208, 72 (3).
Blouet, Parenteral Preparations, Challenges in Formulations, Pharmaceutical Outsourcing, Nov. 20, 2016, https://www.pharmoutsourcing.com/Featured-Articles/331618-Parenteral-Preparations-Challenges-in-Formulations/,.
International Search Report and Written Opinion for PCT/US2018/02305, dated Jun. 9, 2108, 13 pages.
Musiime, et al., Adherence to Highly Active Antiretroviral Treatment in HIV-Infected Rwandan Women, PLOS one, 2011, 1-6, 6 (11).
Rajoli, R.K.R. et al., Physiologically Based Pharmacokinetic Modelling to Inform Development of Intramuscular Long-Acting Nanoformulations for HIV, Clinical Pharmacokinetics, 2015, 639-650, 54 (6).
Spreen, W.R. et al., Long-acting injectable antiretrovirals for HIV treatment and prevention, Current Opinion in HIV and AIDS, 2013, 565-571, 8 (6).
Van't Klooster, et al., Pharmacokinetics and Disposition of Rilpivirine (TMC278), Antimicrobial Agents and Chemotherapy, May 2010, pp. 2042-2050, vol. 54.

*Primary Examiner* — Emily A Bernhardt
(74) *Attorney, Agent, or Firm* — Carol S. Quagliato; John C. Todaro (57) ABSTRACT

The instant invention provides pharmaceutical formulations for a long acting injectable drug product comprising a suspension of doravirine for parenteral administration via intramuscular or subcutaneous routes. The drug product can be used for the treatment or prophylaxis of infection by HIV or for the treatment, prophylaxis, or delay in the onset of AIDS (acquired immunodeficiency syndrome) or ARC (AIDS related complex).

18 Claims, 5 Drawing Sheets

FORMULATION FOR PARENTERAL ADMINISTRATION

BACKGROUND OF THE INVENTION

The development of highly active antiretroviral therapy (HAART) in the mid 1990's transformed the clinical care of human immunodeficiency virus (HIV) type infection. HAART regimens have proven to be highly effective treatments, significantly decreasing HIV viral load in HIV-infected patients, thereby slowing the evolution of the illness and reducing HIV-related morbidity and mortality. Yet, the treatment success of HAART is directly related to adherence to the regimen by the patient. Unless appropriate levels of the antiretroviral drug combinations are maintained in the blood, viral mutations will develop, leading to therapy resistance and cross-resistances to molecules of the same therapeutic class, thus placing the long-term efficacy of treatments at risk. Various clinical studies have shown a decline in treatment effectiveness with relatively small lapses in adherence. A study by Musiime found that 81% of patients with more than 95% adherence demonstrated viral suppression, while only 50% of patients who were 80-90% adherent were successful. See, Musiime, S., et al., Adherence to Highly Active Antiretroviral Treatment in HIV-Infected Rwandan Women. *PLOS one* 2011, 6, (11), 1-6. Remarkably, only 6% of patients that were less than 70% adherent showed improvements in viral markers. Thus, low adherence is a leading cause of therapeutic failure in treatment of HIV-1 infection.

Nonetheless, adherence rates to the HAART regimens continue to be far from optimal. Various characteristics of HAART make adherence particularly difficult. Therapeutic regimens are complex, requiring multiple drugs to be taken daily, often at different times of the day, and many with strict requirements on food intake. Many HAART medications also have unpleasant side effects, including nausea, diarrhea, headache, and peripheral neuropathy. Social and psychological factors can also negatively impact adherence. Patients report that forgetfulness, lifestyle factors, including fear of being identified as HIV-positive, and therapy fatigue over life-long duration of treatment all contribute to adherence lapses.

New HIV treatment interventions aim to improve adherence by reducing the complexity of treatments, the frequency of the dosages, and/or the side effects of the medications. Long-acting injectable (LAI) drug formulations that permit less frequent dosing, on the order of a month or longer, are an increasingly attractive option to address adherence challenges. However, the majority of approved and investigational antiretroviral agents are not well suited for reformulation as long-acting injectable products. In large part, this is due to suboptimal physicochemical properties limiting their formulation as conventional drug suspensions, as well as insufficient antiviral potency resulting in high monthly dosing requirements. Even for cabotegravir or rilpivirine, two drugs being studied as long-acting injectable formulations, large injection volumes and multiple injections are required to achieve pharmacokinetic profiles supportive of monthly dosing. See, e.g., Spreen, W. R., et al., Long-acting injectable antiretrovirals for HIV treatment and prevention. *Current Opinion in Hiv and Aids* 2013, 8, (6), 565-571; Rajoli, R. K. R., et al., Physiologically Based Pharmacokinetic Modeling to Inform Development of Intramuscular Long-Acting Nanoformulations for HIV. *Clinical Pharmacokinetics* 2015, 54, (6), 639-650; Baert, L., et al., Development of a long-acting injectable formulation with nanoparticles of rilpivirine (TMC278) for HIV treatment. *European Journal of Pharmaceutics and Biopharmaceutics* 2009, 72, (3), 502-508; Van't Klooster, G., et al., Pharmacokinetics and Disposition of Rilpivirine (TMC278) Nanosuspension as a Long-Acting Injectable Antiretroviral Formulation. *Antimicrobial Agents and Chemotherapy* 2010, 54, (5), 2042-2050.

Doravirine is a non-nucleoside reverse transcriptase inhibitor and is currently in clinical development for oral administration. Synthesis of doravirine and the ability of doravirine to inhibit HIV reverse transcriptase is illustrated in U.S. Pat. No. 8,486,975, which is hereby incorporated by reference in its entirety. Doravirine has the following structural formula:

Given the chronic nature of HIV therapy and sub-optimal outcomes in terms of the fraction of infected patients seeing virological suppression, a novel formulation approach capable of delivering extended-duration pharmacokinetic characteristics for doravirine at practical injection volumes and with a limited number of injections is highly desirable. Such formulations would provide an alternative treatment option that could be useful for improving treatment adherence in certain patient populations.

SUMMARY OF THE INVENTION

The instant invention provides pharmaceutical compositions and formulations for long acting injectable (LAI) drug products for parenteral administration via intramuscular (IM) or subcutaneous (SC) routes comprising a suspension of doravirine. The drug product can be used for the treatment of, or prophylaxis of infection by, HIV or for the treatment, prophylaxis, or delay in the onset of AIDS (acquired immunodeficiency syndrome) or ARC (AIDS related complex).

DETAILED DESCRIPTION OF THE INVENTION

Doravirine can exist in more than one polymorphic crystal form. The anhydrous crystalline Form II of doravirine (referred to as D-AHII herein) is used in the composition described herein. D-AHII can be obtained according to the procedures described in WO2014052171 (WO'171) and U.S. Pat. No. 9,150,539, published on Apr. 3, 2014, and Oct. 6, 2015 respectively, both incorporated herein by reference in their entirety.

As described in WO'171, the AHII form of doravirine is crystallized from solvent mixtures, for example, DMAc/water and NMP/ethanol, depending on impurity rejection needs vs. process yield. Controlling the crystal growth kinetics is performed to avoid formation of a less stable but kinetically favored crystalline form of doravirine (the less stable form is referred to as Anhydrous Form I in WO'171), and to generate the desired particle size kinetics. Additional particle size reduction techniques such as milling may also be utilized to reduce the particle size further.

Doravirine has a pKa of 9.47 and, accordingly, the aqueous solubility of this compound is extremely limited at physiologically relevant pH ranges. The solubility of D-AHII in water and pH buffers at 25° C. is shown in Table 1.

TABLE 1

Solubility of doravirine (D-AHII) at 25° C. (7 Days)

| Buffer | pH (initial) | pH (final) | Solubility (µg/mL) |
|---|---|---|---|
| Water | — | 6.73 | 6.30 |
| 50 mM pH 2 Phosphate Buffer | 2 | 2.16 | 4.10 |
| 50 mM pH 3 Phosphate Buffer | 3 | 3.11 | 3.43 |
| 50 mM pH 4 Acetate Buffer | 4 | 4.15 | 3.70 |
| 50 mM pH 5 Acetate Buffer | 5 | 4.95 | 5.10 |
| 50 mM pH 6.5 Phosphate Buffer | 6.5 | 6.62 | 4.3 |
| 50 mM pH 7 Phosphate Buffer | 7 | 7.13 | 2.70 |
| 50 mM pH 8 Phosphate Buffer | 8 | 7.89 | 4.00 |
| 50 mM pH 9 Tris Buffer | 9 | 8.56 | 4.57 |
| 50 mM pH 10 Borate Buffer | 10 | 9.47 | 4.33 |

Due to the extremely low aqueous solubility of doravirine, a slow dissolving suspension formulation administered intramuscularly or subcutaneously at a frequency of QM (once monthly) to QQ (once quarter-yearly) was considered. Based on prior knowledge in this field of art, it would be expected that, at a given dose, an LAI nanosuspension of a pharmaceutical active ingredient would lead to a higher input rate and shorter duration of release upon administration to a subject as compared to a microsuspension [see, e.g., Baert, L., et al., Development of a long-acting injectable formulation with nanoparticles of rilpivirine (TMC278) for HIV treatment, *European Journal of Pharmaceutics and Biopharmaceutics* 2009, 72, (3), 502-508]. However, in an effort to develop a suspension product comprising D-AHII suitable for QM to QQ administration via an intramuscular (IM) and/or subcutaneous (SC) administration route, we have discovered that microsuspension and nanosuspension formulations prepared using D-AHII and injected intramuscularly or subcutaneously provide sustained and comparable plasma exposure in preclinical species (rabbit and dog).

As shown in Table 2, the nanosuspension formulation of D-AHII exhibited a comparable PK profile to the MPS 8 µm and MPS 2 µm microsuspension in the dog PK study. The pharmacokinetic exposure after IM injections of D-AHII thus demonstrated: (1) a particle size independent PK profile and a desired input rate in a range from a nanosuspension from about 100 nm ($D_{10}$) to about 20 µm ($D_{90}$) (Table 2), and (2) a particle size dependent PK profile as the PSD increases beyond 20 µm (Table 2).

TABLE 2

Pharmacokinetic parameters (mean) in dogs and rabbits following intramuscular administration of D-AHII suspensions at a dose of 200 mg/subject (n ≥ 4)

| | Suspension Particle Size Distribution (µm) | | | | AUC | $C_{max}$ | $T_{max}$ | $C_{32d}$ | $C_{trough}$ |
|---|---|---|---|---|---|---|---|---|---|
| | $D_{10}$ | $D_{50}$ | $D_{90}$ | Species | (µM × day) | (µM) | (day) | (µM) | (µM) |
| Nanosuspension | 0.10 | 0.27 | 0.46 | Dog | 99.74 | 3.0 | 11 | 1.3 | 0.17 |
| Microsuspension, MPS 2 µm | 0.8 | 1.8 | 3.7 | Dog | 70.72 | 3.64 | 7 | 0.62 | 0.16 |
| Microsuspension, MPS 8 µm | 2.6 | 7.6 | 15.3 | Dog | 69.54 | 2.98 | 11 | 0.67 | 0.2 |
| Microsuspension, MPS 27 µm | 5.3 | 27.6 | 62.7 | Rabbit | 20.47 | 0.34 | 44 | 0.21 | 0.22 |
| Microsuspension, MPS 8 µm | 2.6 | 7.6 | 15.3 | Rabbit | 32.37 | 0.6 | 15 | 0.26 | 0.13 |
| Microsuspension, MPS 2 µm | 0.8 | 1.8 | 3.7 | Rabbit | 24.96 | 0.64 | 12 | 0.49 | 0.15 |

The PK profile suggests a single dose of 20% D-AHII nanosuspension or microsuspension can provide sustained plasma levels for at least one month. Although particle size distribution influenced the initial release/input rate over the first few days, the sustained profiles were comparable for formulations with PSD ranging from about 100 nm ($D_{10}$ for nanosuspension) to about 20 μm ($D_{90}$ for 8 μm microsuspension) with specific surface area ranging from 22.2 m²/g (calculated for nanosuspension with MPS of 270 nm) to 1.8 m²/g (measured for microsuspension with MPS of 8 μm). For example, the MPS 8 micron suspension provided sustained plasma levels of doravirine at therapeutically relevant concentrations for humans (78 nM).

Figure 1:
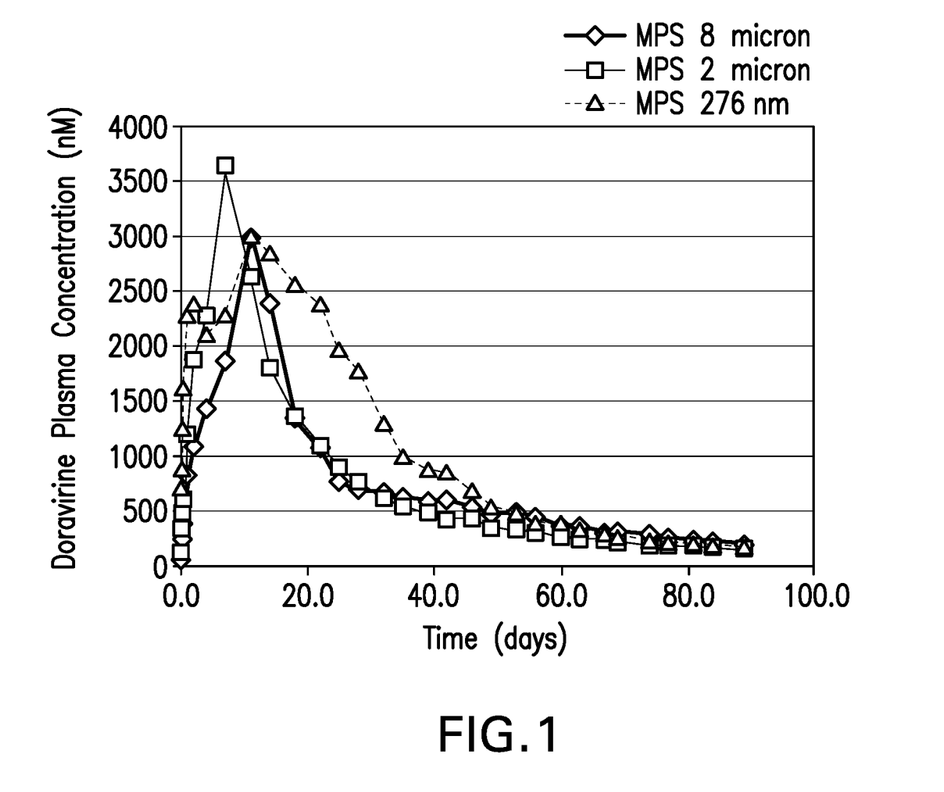
FIG. 1 shows the pharmacokinetic profile in dogs with D-AHII suspensions (20% w/v) of varying particle size distribution administered intramuscularly (200 mg, 1 mL).
Figure 2:
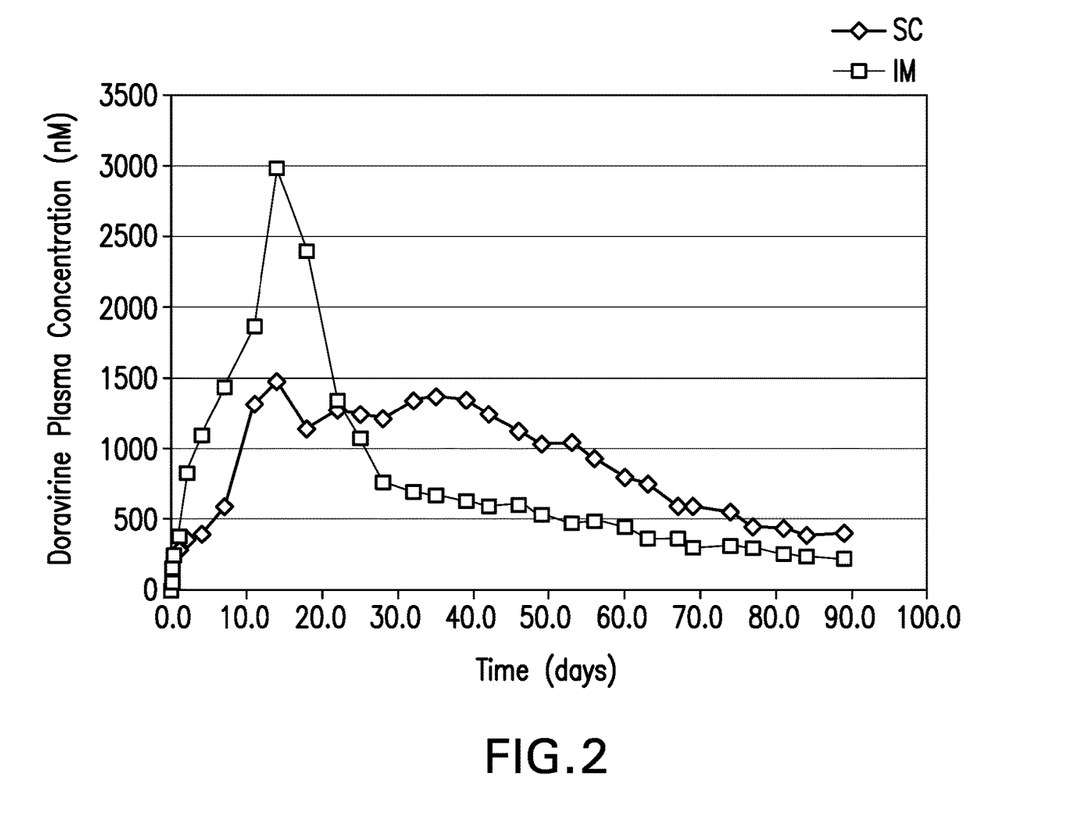
FIG. 2 shows the pharmacokinetic profile in dogs with D-AHII microsuspension (MPS 8 µm, 20% w/v) comparing subcutaneous (SC) and intramuscular (IM) routes of administration (200 mg, 1 mL).
Figure 3:
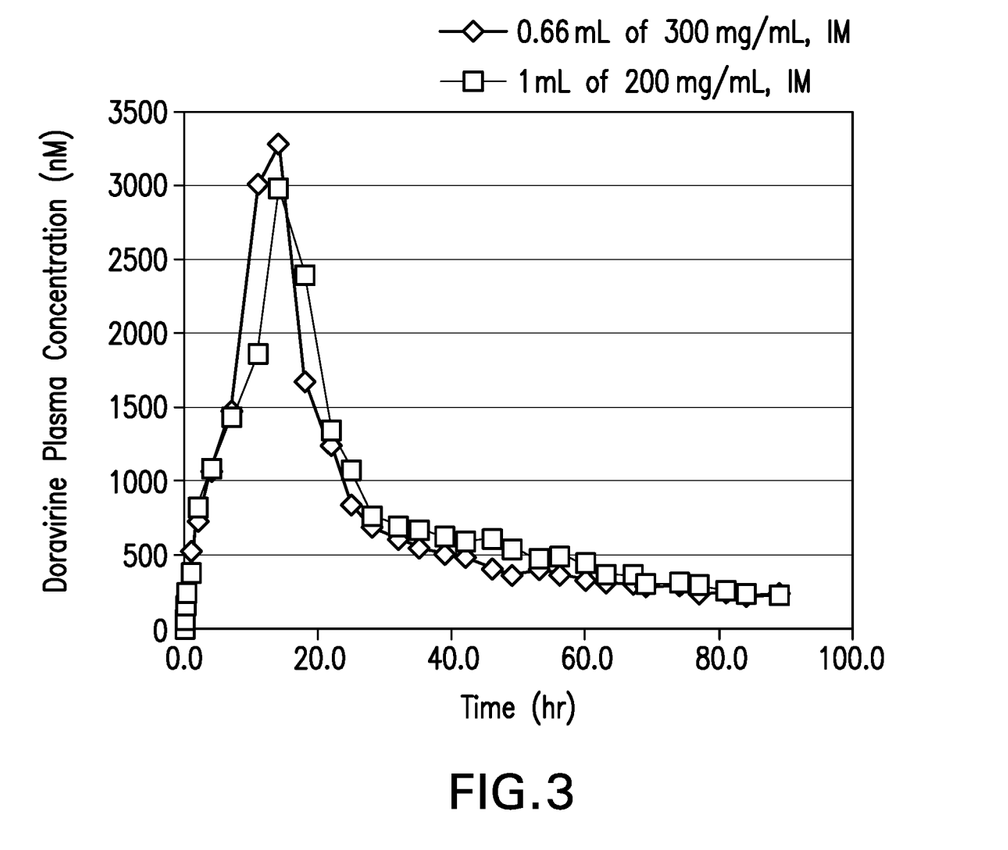
FIG. 3 shows the pharmacokinetic profile in dogs with D-AHII microsuspension (MPS 8 µm, 200 mg) administered intramuscularly as 20% w/v (1 mL) or 30% w/v (0.66 mL) suspensions.
Figure 4:
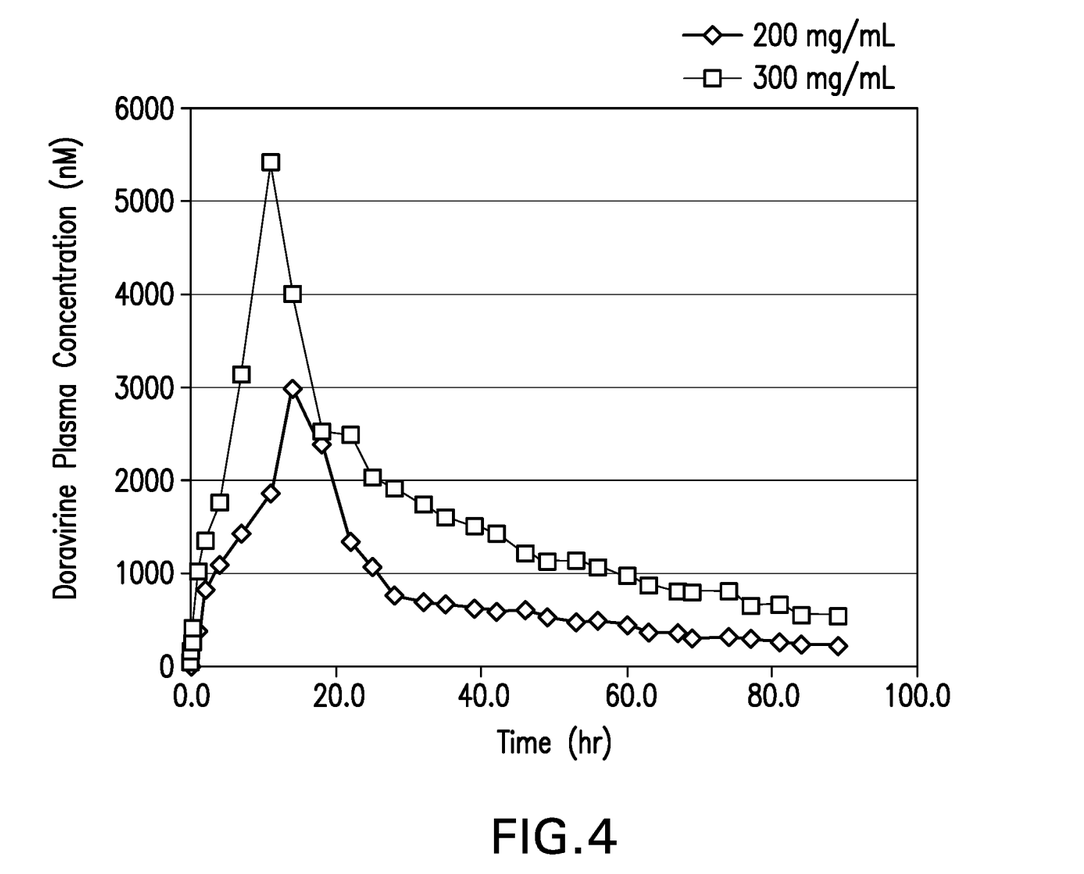
FIG. 4 shows the pharmacokinetic profile in dogs of D-AHII microsuspension (MPS 8 µm, 20% w/v) administered intramuscularly at a dose of 200 mg and a dose of 300 mg.
Figure 5A:
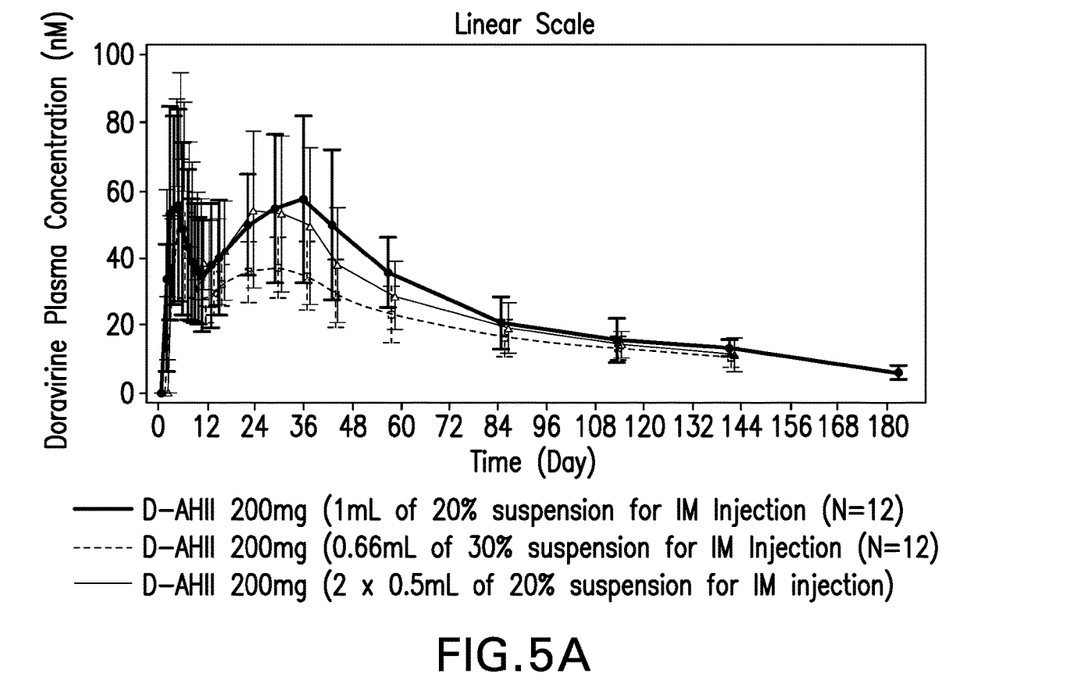
FIG. 5 shows the mean (±SD) plasma D-AHII profiles following 200 mg fixed doses of two formulations of D-AHII administered as single intramuscular injections or as two intramuscular injections in healthy human subjects [0 to 183 days].
Figure 5B:
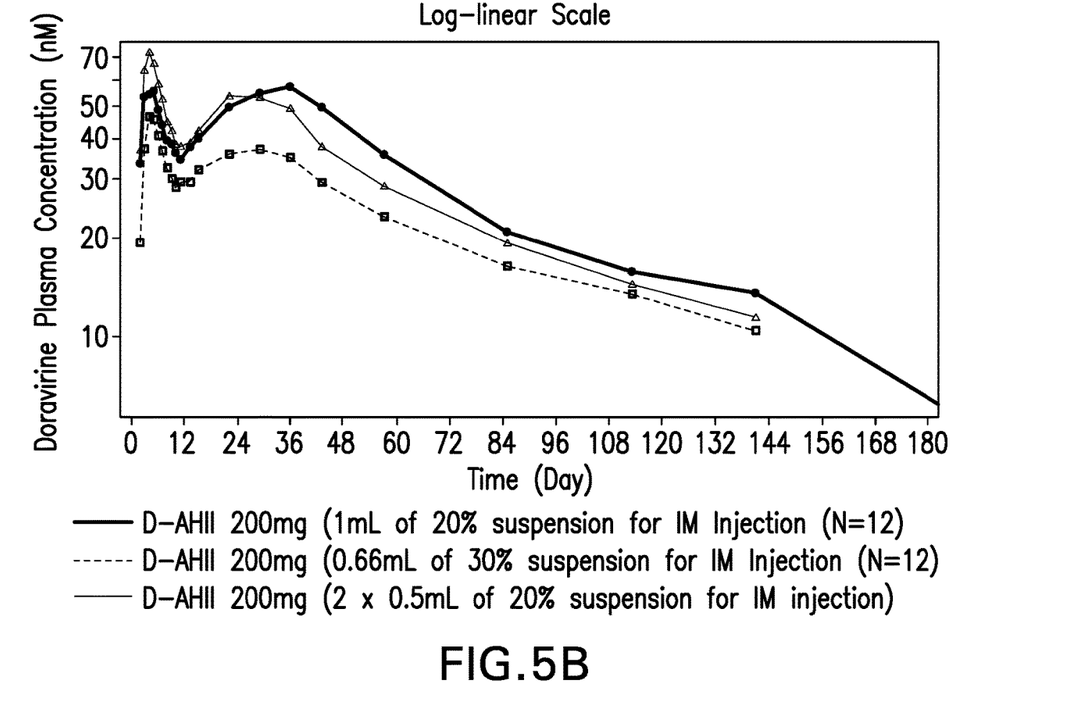

Hence, we have discovered that suspensions of D-AHII with specific surface area from 22.2 m²/g to 1.8 m²/g and particle size from about 100 nm ($D_{10}$) up to and including about 20 μm ($D_{90}$), when administered intramuscularly or subcutaneously, provide a PK profile acceptable for at least QM administration in mammals, particularly humans. Unexpectedly, nanosuspensions with a median particle size of 200 nm exhibit similar PK profiles when compared to the MPS 8 micron suspension. In addition both SC and intramuscular IM routes of administration provide comparable duration of sustained release (FIG. 1). Modulation of suspension concentration did not change the sustained release profile significantly (FIG. 2) while an increase in dose proportionately increased the plasma concentration over the duration of release (FIG. 3).

As shown in Table 3, the microsuspension (MPS 8 μm) formulation of D-AHII exhibited a comparable PK profile after Intramuscular administration of 20% and 30% suspension at a dose of 200 mg. The pharmacokinetic exposure after IM injections of D-AHII thus demonstrated: (1) a suspension concentration independent PK profile, and (2) Comparable PK profile between a single 1 mL injection and two 0.5 mL injections (Table 3).

TABLE 3

D-AHII Plasma Pharmacokinetic Profile Following 200 mg Fixed Dose of microsuspension (MPS 8 um) Administered as Single Intramuscular Injections or as Two Intramuscular Injections in Healthy Subjects

| Parameter | Trt | ArithMean | SD | CV % | N |
|---|---|---|---|---|---|
| AUC0-last | A | 4.34 | 1.12 | 25.7 | 12 |
| (Day · nM) | B | 3.14 | 0.824 | 26.3 | 12 |
|  | C | 4.27 | 1.09 | 25.6 | 12 |
| Cmax | A | 72.5 | 28.3 | 39.1 | 12 |
| (nM) | B | 51.6 | 12.2 | 23.7 | 12 |
|  | C | 76.8 | 23.2 | 30.2 | 12 |
| Tmax | A | 20.33 | 18.65 | 91.7 | 12 |
| (Day) | B | 14.84 | 15.91 | 107.2 | 12 |
|  | C | 10.42 | 11.59 | 111.3 | 12 |
| t½† | A | 49.92 | 25.45 | 51.0 | 11 |
| (Day) | B | 67.29 | 44.14 | 65.6 | 11 |
|  | C | 53.81 | 20.26 | 37.6 | 11 |

†Terminal elimination parameters were not selected for two subjects due to an upward trend in the terminal elimination phase to the last sampling time point; terminal elimination parameters were not selected one subject due to an insufficient number of data points in the elimination phase (one subject in each treatment).
SD = Standard deviation
CV % = Coefficient of variation (100 * SD/Mean)
N = Number of non-missing data
Treatment A: D-AHII 200 mg (1 mL of 20% suspension for IM injections)
Treatment B: D-AHII 200 mg (0.66 mL of 30% suspension for IM injections)
Treatment C: D-AHII 200 mg (2 × 0.5 mL of 20% suspension for IM injections)

We have also discovered that a D-AHII nanosuspension formulation is particularly well stabilized by Vitamin E TPGS, a non-ionic surfactant and particularly at high drug loads (up to 40% w/w of D-AHII). Vitamin E TPGS is a novel excipient for long acting parenteral (LAP) use. Multiple surfactants of different types were tested as nanosuspension stabilizers including non-ionic surfactants such as poloxamers 188, 338, and 407, polysorbate 20 and polysorbate 80, and ionic surfactants such as sodium deoxycholate, sodium taurocholate, and sodium docusate. These surfactants alone or in combination with other surfactants demonstrated inferior stabilization compared to Vitamin E TPGS that is acceptable for the sterile applications. Additionally, the 4% w/v Vitamin E TPGS based vehicle was tested in dogs and rats for safety and no adverse effects were reported.

It has been further discovered that a particle size distribution with a $D_{50}$ of approximately 200 nm and $D_{90}$<500 nm for D-AHII in the formulation can be produced by wet media milling, which would not be viable in the absence of the formulation components described herein.

Composition:

The composition includes the D-AHII at a concentration ranging from 1% to 30%, or from 10% to 30%, or from 20% to 30%, or particularly 20% or 30%.

The composition includes a surfactant, for example a pharmaceutically acceptable surfactant approved for intramuscular use. For example, the surfactant may be non-ionic or ionic and may include one or more of polysorbate 80, polysorbate 20, poloxyamer 188, Vitamin E TPGS, docusate sodium or sodium deoxycholate. Preferably the surfactant is polysorbate 80 or Vitamin E TPGS. The D-AHII:surfactant weight ratio may be from 150:1 to 1:1. Preferably the D-AHII:surfactant weight ratio is 150:1 to 20:1 for microsuspensions, and 7.5:1 to 5:1 for nanosuspensions. The composition may include one surfactant or a combination of two or more surfactants.

The composition further includes a pharmaceutically acceptable viscosity modifying agent, to enhance product stability and permit an acceptable shelf life. The viscosity modifying agent may be a higher molecular weight (higher than MW>1000, particularly >3000) polyethylene glycol (PEG) such as polyethylene glycol 3350 (PEG 3350) or a cellulose derivative such as sodium carboxymethylcellulose. Preferably the viscosity modifying agent is PEG 3350. The concentration of the viscosity modifying agent may be from 0.1 wt % to 3.0 wt %. The viscosity of the suspension may range from 1.4 cP to 1220 cP (at shear rate of 100/s). Preferably, the viscosity of the suspending vehicle may be from 1.4 cP to 1.6 cP for the microsuspension, and from 325 cP to 1220 cP (at shear rate of 100/s) for the nanosuspension. The nanosuspension demonstrates a shear-thinning thixotropic behavior with the viscosity of the nanosuspension ranging from 325 cP to 1220 cP at a shear rate of 100/s, and 610 cP to 2242 cP at a shear rate of 50/s. The composition may include one viscosity modifying agent or a combination of two or more viscosity modifying agents.

The composition may optionally include a pharmaceutically acceptable buffering agent to control product pH. A suitable pH for the D-AHII suspension is from 4 to 9, and particularly from 6 to 8, or more particularly a pH of 7. The buffering agent, when used, may be a phosphate buffering agent (e.g., monobasic sodium phosphate/dibasic sodium phosphate) to achieve suspensions having a pH from 4 to 9, and particularly from 6 to 8, or more particularly a pH of 7. The concentration of the buffering agent in the suspension compositions of this disclosure is from zero (when no buffering agent is used) up to 50 mM; for example, if used, the concentration of the buffering agent is above zero mM (e.g., 0.1 mM) up to 50 mM. Preferably the concentration of the buffering agent is 10 mM for a microsuspension. Preferably the concentration of the buffering agent is 0 to 10 mM for a nanosuspension; for example, if used, the concentration of the buffering agent is above zero mM (e.g., 0.1 mM) up to 10 mM.

The composition may further include a pharmaceutically acceptable tonicity modifier for parenteral use such as sugars (dextrose, mannitol, sucrose, trehalose) and salts (sodium chloride). The tonicity modifier would adjust the osmolality of the suspension in the range from 280 mOsm/kg to 700 mOsm/kg. The tonicity modifier may be, for example but not limited to, mannitol or sodium chloride for the microsuspension. For example, the concentration in the suspension can be 5.0% for mannitol and 0.9% for sodium chloride in the microsuspension. Preferably the tonicity modifier is sodium chloride for the microsuspension. Preferably the concentration in the suspension of sodium chloride is 0.9% for the microsuspension. The concentration can be 0.9% for sodium chloride, 10% to 20% for trehalose or sucrose, with a sugar to drug ratio of 0.5:1.0 in the nanosuspension. Preferably, the concentration of trehalose is 20% with a sugar to drug ratio of 1:1 for the nanosuspension.

Certain non-limiting embodiments of this invention are as follows.

In Embodiment 1 is an LAI suspension composition comprised of D-AHII having a specific surface area from 22.2 $m^2/g$ to 1.8 $m^2/g$.

In Embodiment 2 is an LAI suspension composition comprised of D-AHII having a particle size from about 100 nm ($D_{10}$) to about 20 μm ($D_{90}$).

In Embodiment 2A is an LAI suspension composition comprised of D-AHII having a median particle size from about 200 nm to about 8 μm.

In Embodiment 2B is the composition of Embodiment 2 or 2A wherein the D-AHII has a specific surface area from 22.2 $m^2/g$ to 1.8 $m^2/g$.

In Embodiment 3 is the LAI suspension composition of any one of Embodiments 1, 2, 2A or 2B comprised of D-AHII in a concentration range from 1% to 30%; or a concentration range from 10% to 30% (Embodiment 3A); or a concentration range from 20% to 30% (Embodiment 3B); or a concentration of 20% or 30% (Embodiment 3C).

In Embodiment 4 is the LAI suspension composition of any one of Embodiments 1, 2, 2A, 2B, 3, 3A, 3B or 3C wherein the viscosity of the suspending vehicle is in the range from 1.4 cP to 1220 cP.

In Embodiment 4A is the composition of any one of Embodiments 1, 2, 2A, 2B, 3, 3A, 3B, 3C or 4, further comprising a viscosity modifying agent which is a higher molecular weight PEG or a cellulose derivative, wherein the concentration of the viscosity modifying agent is from 0.1 wt % to 3.0 wt %.

In Embodiment 4B are each of the compositions encompassed by Embodiments 4 or 4A wherein the viscosity modifying agent is PEG 3350 or sodium carboxymethylcellulose.

In Embodiment 5 is the LAI suspension composition of any one of Embodiments 1, 2, 2A, 2B, 3, 3A, 3B, 3C, 4, 4A or 4B further comprising one or more surfactants selected from polysorbate 80, polysorbate 20, poloxyamer 188, Vitamin E TPGS, docusate sodium or sodium deoxycholate.

In Embodiment 5A are each of the compositions encompassed by Embodiment 5 wherein the D-AHII:surfactant weight ratio is from 150:1 to 1:15.

In Embodiment 6 is the LAI suspension composition of any one of Embodiments 1, 2, 2A, 2B, 3, 3A, 3B, 3C, 4, 4A, 4B, 5, 5B or 5C further comprising a phosphate buffering agent for adjusting the composition to pH 7.

In Embodiment 6A are each of the compositions encompassed by Embodiment 6 wherein the concentration of the buffering agent is from 0 to 50 mM.

In Embodiment 7 is the LAI suspension composition of any one of Embodiments 1, 2, 2A, 2B, 3, 3A, 3B, 3C, 4, 4A, 4B, 5, 5A, 6 or 6A, further comprising a tonicity modifier for parenteral use such as one or more sugars (for example dextrose, mannitol, sucrose or trehalose) or salts (for example, sodium chloride).

In Embodiment 8 is the LAI suspension composition of any of Embodiments 1, 2, 2A, 2B, 3, 3A, 3B, 3C, 4, 4A, 4B, 5, 5A, 6, 6A or 7 wherein the suspension is a microsuspension.

In Embodiment 8A are each of the microsuspension compositions encompassed by Embodiment 8 wherein the D-AHII has a median particle size of about 2 μm to about 8 μm, or more particularly the median particle size is about 2 μm or about 8 μm.

In Embodiment 9 are each of the microsuspension compositions encompassed by Embodiment 8 or 8A wherein the viscosity of the suspending vehicle is from 1.4 cP to 1.6 cP.

In Embodiment 10 are each of the microsuspension compositions encompassed by Embodiment 8 or 8A or 9 wherein the suspension is a microsuspension, further comprising one or more surfactants selected from polysorbate 80, polysorbate 20, poloxyamer 188, Vitamin E TPGS, docusate sodium or sodium deoxycholate, wherein the D-AHII:surfactant weight ratio is from 150:1 to 20:1.

In Embodiment 11 are each of the microsuspension compositions encompassed by Embodiment 8, 8A, 9 or 10 further comprising a phosphate buffering agent for adjusting the composition to pH 7, wherein the concentration of the buffering agent is 10 mM.

In Embodiment 11A are each of the microsuspension compositions encompassed by Embodiment 8, 8A, 9, 10 or 11 wherein the phosphate buffering agent is monobasic sodium phosphate or dibasic sodium phosphate or a combination thereof.

In Embodiment 12 are each of the microsuspension compositions encompassed by Embodiment 8, 8A, 9, 10, 11 or 11A further comprising a tonicity modifier which is mannitol or sodium chloride or a combination of both, and wherein particularly it is sodium chloride.

In Embodiment 12A are each of the microsuspension compositions encompassed by Embodiment 8, 8A, 9, 10, 11, 11A or 12 wherein the tonicity modifier is mannitol and its concentration in the microsuspension is 5.0%, or the tonicity modifier is sodium chloride and its concentration in the microsuspension is 0.9%; and particularly wherein the microsuspension is comprised of 0.9% concentration of sodium chloride.

In Embodiment 13 is the LAI suspension composition of any of Embodiments 1, 2, 2A, 2B, 3, 3A, 3B, 3C, 4, 4A, 4B, 5, 5A, 6, 6A, or 7 wherein the suspension is a nanosuspension.

In Embodiment 13A are each of the nanosuspension compositions encompassed by Embodiment 13 wherein the D-AHII has a specific surface area from about 60 $m^2/g$ to about 20 $m^2/g$.

In Embodiment 13B are each of the nanosuspension compositions encompassed by Embodiment 13 or 13A wherein the D-AHII has a median particle size from about 100 nm to about 300 nm.

In Embodiment 14 are each of the nanosuspension compositions encompassed by Embodiment 13, 13A or 13B wherein the viscosity of the suspending vehicle is from 325 cP to 1220 cP (at shear rate of 100/s).

Embodiment 15 are each of the nanosuspension compositions encompassed by Embodiment 13, 13A, 13B or 14, wherein the suspension is a nanosuspension, further comprising one or more surfactants selected from polysorbate 80, polysorbate 20, poloxyamer 188, Vitamin E TPGS, docusate sodium or sodium deoxycholate, wherein the D-AHII:surfactant weight ratio is from 7.5:1 to 5:1.

In Embodiment 16 are each of the nanosuspension compositions encompassed by Embodiment 13, 13A, 13B, 14 or 15 (1) wherein no buffering agent is used, or (2) further comprising a phosphate buffering agent for adjusting the composition to pH 7, and if a buffering agent is used, the concentration of the buffering agent is from 0.1 mM to 10 mM.

In Embodiment 17 are each of the nanosuspension compositions encompassed by Embodiment 13, 13A, 13B, 14, 15 or 16 further comprising a tonicity modifier which is sucrose, trehalose or sodium chloride, and wherein particularly it is trehalose.

In Embodiment 17A are each of the nanosuspension compositions encompassed by Embodiment 13, 13A, 13B, 14, 15, 16 or 17 wherein the tonicity modifier is sucrose and its concentration in the nanosuspension is from 10% to 20%, or the tonicity modifier is trehalose and its concentration in the nanosuspension is from is from 10% to 20%, or the tonicity modifier is sodium chloride and its concentration in the nanosuspension is 0.9%; and the sugar to D-AHII ratio is 0.5:1.0.

In Embodiment 17B are each of the nanosuspension compositions encompassed by Embodiment 13, 13A, 13B, 14, 15, 16, 17 or 17A wherein the concentration of trehalose is 20% with a sugar to D-AHII ratio of 1:1.0.

In Embodiment 18 are each of the compositions encompassed by each of the foregoing Embodiments 1 through 17B, wherein a single unit dosage for QM or QQ administration of the LAI composition is comprised of ≥200 mg of D-AHII, or particularly from 200 mg to 1200 mg of D-AHII, or more particularly 200 mg of D-AHII.

The pharmaceutical compositions comprised of D-AHII of this disclosure may be used for the treatment or prophylaxis of infection by HIV, for the inhibition of HIV reverse transcriptase, for the treatment, prophylaxis, or delay in the onset of AIDS in a subject in need thereof, which comprise administering to the subject an effective amount of a compound of the disclosure or a pharmaceutically acceptable salt thereof.

The pharmaceutical compositions of this invention comprising D-AHII further comprises an effective amount of one or more additional anti-HIV agents selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Acronyms, abbreviations and definitions of some terms used herein include the following:

"about" is +/−20% of the defined value. Some non-limiting examples are:
"about 100 nm" includes a range from 80 to 120 nm;
"about 200 nm" includes a range from 160 to 240 nm;
"about 20 μm" includes a range from 16 to 24 μm;
"about 8 μm" includes a range from 6.4 to 9.6 μm
D-AHII = doravirine crystalline Form II
API = active pharmaceutical ingredient
cP = centipoise = measurement unit of dynamic viscosity in the centimeter gram second (CGS) system of units.
cryo-SEM = cryo-scanning electron microscopy
DMAc = dimethyl acetamide; NMP = N-methyl-pyrrolidinone
e.g. = for example
mL = milliliters; mM = millimolar; μM = micromolar
nm = nanometer; μm = micrometer, micron
$m^2/g$ = specific surface area units
MPS = median particle size
PK = pharmacokinetic
PSD = particle size distribution
/s = units of shear rate
w/v = weight/volume
WFI = water for injection
$D_{10}$, $D_{50}$, $D_{90}$ - when measuring particle size distribution (PSD):
D represents the diameter of particles, and $D_{50}$ means a cumulative 50% point of diameter (or 50% pass particle size); $D_{50}$ is also referred to as average particle size or median diameter; $D_{10}$ means a cumulative 10% point of diameter, $D_{90}$ means a cumulative 90% point of diameter
Nanosuspension = suspension containing particles having a median particle size of less than one micrometer
Microsuspension = suspension containing particles having a median particle size equal to or greater than one micrometer and less than one millimeter
Suspending vehicle = all components of the composition excluding the D-AHII
Vitamin E TPGS or VitE TPGS = D-α-tocopheryl polyethylene glycol 1000 succinate

EXAMPLES

Microsuspensions:

D-AHII microsuspension formulations were prepared in the following manner: D-AHII was dry jet-milled or pin-milled or spiral milled to the desired particle size of crystalline phase (D-AHII). Suspension media components (surfactants, viscosity modifiers, buffers, tonicity modifiers) were added in the desired amounts to water-for-injection and stirred until dissolved. The D-AHII was added to the suspension medium and stirred until a uniform suspension was made. Additional water-for-injection was added to bring the suspension to the desired volume.

For each of the microsuspensions in Examples 1 and 2, approximately 70 mL of water-for-injection was added to a vessel and polyethylene glycol (3 mg) with molecular weight 3350 was added to the vessel and stirred until dissolved. Then polysorbate 80 (1 g) was added to the vessel and stirred until dissolved. Next, phosphate buffer (10 mM) was added to the vessel and stirred until dissolved, then sodium chloride (900 mg) was added to the vessel and stirred until dissolved. The solution was filtered through a 0.22 μm filter. Pin-milled D-AHII (1000 mg, $D_{50}$=1.8 μm) was added to the vessel and stirred until a uniform suspension was achieved. The pH was adjusted to 7.0±0.5 with hydrochloric acid or sodium hydroxide as needed. Water-for-injection was added to the suspension as needed to bring the final volume to 100 mL.

In the following Examples 1-9, particle size distribution refers to D-AHII particle size distribution in microsuspensions and nanosuspensions.

Example 1

| Ingredient | Quantity |
|---|---|
| D-AHII | 30.0% (w/v) |
| Polyethylene glycol 3350 | 3% (w/v) |

-continued

| Ingredient | Quantity |
| --- | --- |
| Polysorbate 80 | 0.2% (w/v) |
| Phosphate buffer | 10 mM |

-continued

| Ingredient | Quantity |
| --- | --- |
| Water for Injection | QS to 100% |
| pH | 7.0 |
| Other | |
| Particle size distribution ($D_{10}/D_{50}/D_{90}$) | 2.58/7.61/15.33 |
| Specific surface area ($m^2/g$) | 1.82 |

Example 2

| Ingredient | Quantity |
| --- | --- |
| D-AHII | 20.0% (w/v) |
| Polyethylene glycol 3350 | 3.0% (w/v) |
| Polysorbate 80 | 1.0% (w/v) |
| Sodium chloride | 0.9% (w/v) |
| Phosphate buffer | 10 mM |
| Water for Injection | QS to 100% |
| pH | 7.0 |
| Other | |
| Particle size distribution ($D_{10}/D_{50}/D_{90}$) | 0.8/1.8/3.7 |
| Specific surface area ($m^2/g$) | 9.8 |

Nanosuspensions:

D-AHII nanosuspension formulations in the following Examples were prepared in the following manner: D-AHII starting material was wet milled using low energy or high energy mill with the target particle size distribution of about 200 nm ($D_{50}$) with a $D_{90}$ not greater than 500 nm. The inactive ingredients were dissolved in water by sequential addition and sterile filtered. To a specified amount of the prepared vehicle, the target weight of D-AHII was added and slurried to ensure complete wetting of the added D-AHII. The prepared slurry was wet milled using appropriate media (polystyrene or zirconium beads) in a batch or circulation mode per equipment capability. At the end of the milling step the nanosuspension was collected and filled into glass vials for use as is or subjected to lyophilization to freeze-dry the nanosuspension. Examples of nanosuspension compositions are shown in Examples 3-8:

| Components | Example 3 | Example 4 | Example 5 | Example 6 | Example 7 | Example 8 |
| --- | --- | --- | --- | --- | --- | --- |
| Active Pharmaceutical Ingredient Quantity | | | | | | |
| D-AHII | 20% (w/w) | 30% (w/w) | 20% (w/w) | 20% (w/w) | 10% (w/w) | 10% (w/w) |
| Suspending Vehicle Quantity | | | | | | |
| | 80% (w/w) | 70% (w/w) | 80% (w/w) | 80% (w/w) | 90% (w/w) | 90% (w/w) |
| Suspending Vehicle Composition | | | | | | |
| VitE TPGS | 4% (w/w) | 4% (w/w) | 2% (w/w) | 4% (w/w) | 2% (w/w) | 2% (w/w) |
| Phosphate buffer | (10 mM) | (10 mM) | — | — | — | — |
| Sodium chloride | 0.9% (w/w) | — | — | — | — | — |
| Trehalose | — | — | — | 20% (w/w) | — | 10% (w/w) |
| Sucrose | — | — | — | — | 10% (w/w) | — |
| Deoxicholate Na | — | — | 0.25% (w/w) | — | — | — |
| Docusate Na | — | — | 0.1% (w/w) | — | — | — |
| WFI | QS to 100% | QS to 100% | QS to 100% | QS to 100% | QS to 100% | QS to 100% |
| Particle Size Distribution (microns) | | | | | | |
| $D_{10}$ | 0.104 | 0.106 | — | 0.092 | 0.094 | 0.097 |
| $D_{50}$ | 0.276 | 0.251 | 0.174 | 0.138 | 0.147 | 0.149 |
| $D_{90}$ | 0.456 | 0.454 | 0.306 | 0.232 | 0.251 | 0.242 |

Example 9

| Components | Quantity |
| --- | --- |
| Active Pharmaceutical Ingredient | |
| D-AHII | 20% (w/w) |
| Suspending Vehicle (80%) | |
| Vitamin E TPGS | 4% (w/w) |
| Water for Injection | QS to 100% |
| Particle Size distribution (initial, μm) | |
| $D_{10}$ | 0.100 |
| $D_{50}$ | 0.141 |
| $D_{90}$ | 0.225 |

The compositions of Examples 3 through 8 were physically stable for at least 1 month. The composition of Example 9 was monitored on stability for up to 3 months at 5° C. and no particle size growth was recorded (Table 4).

TABLE 4

Nanosuspension (Example 9 composition) physical stability assessment

| Temp (° C.) | PSD (nm) | | | | | |
| --- | --- | --- | --- | --- | --- | --- |
| | 1 month | | | 3 month | | |
| | $D_{10}$ | $D_{50}$ | $D_{90}$ | $D_{10}$ | $D_{50}$ | $D_{90}$ |
| 5 | 90 | 141 | 231 | 104 | 145 | 223 |
| 25 | 98 | 142 | 225 | 107 | 147 | 221 |
| 40 | 105 | 146 | 223 | 107 | 147 | 224 |

The suspension product containing D-AHII may be manufactured as a suspension for administration by injection to a patient, or as a powder to be diluted to prepare the suspension for administration by injection to a patient. A suspension for administration could be made by combining sterile D-AHII (via gamma irradiation or sterile crystallization) and sterile filtered excipients in an appropriate sterile area (e.g., under a class 100 environment). The vehicle and D-AHII would be mixed aseptically into a homogenous suspension and filled into vials under bulk mixing. Lyophilization of the filled suspension may be performed after this step.

A powder for suspension prior to administration could be made leveraging a two vial product image for combination at the time of administration. The vehicle would be compounded, sterile filtered, filled into vials, stoppered and sealed and may or may not be followed by terminal steam sterilization. The D-AHII would be sterilized via gamma irradiation or dry heat after low bioburden and low particulate filling, or sterile crystallized and aseptically filled into vials in an appropriate sterile area (e.g., under a class 100 environment), stoppered and capped.

What is claimed is:

1. A parenteral pharmaceutical composition for intramuscular or subcutaneous administration comprising a suspension of particles of crystalline Form II of doravirine (D-AHII) wherein the particles have a specific surface area within a range from 22.2 m²/g to 1.8 m²/g.

2. The composition of claim 1 wherein the D-AHII has a particle size from about 100 nm ($D_{10}$) to about 20 μm ($D_{90}$).

3. The composition of claim 1 wherein the D-AHII has a median particle size from about 200 nm to about 8 μm.

4. The composition of claim 2 comprised of D-AHII at a concentration range from 1% to 30%.

5. The composition of claim 2 comprised of D-AHII at a concentration range from 10% to 30%.

6. The composition of claim 2 comprised of D-AHII at a concentration range from 20% to 30%.

7. The composition of claim 4 further comprised of a surfactant which is one or more of polysorbate 80, polysorbate 20, poloxyamer 188, Vitamin E TPGS, docusate sodium or sodium deoxycholate.

8. The composition of claim 7 wherein the surfactant is polysorbate 80 or Vitamin E TPGS or a combination of both.

9. The composition of claim 4 wherein the D-AHII: surfactant weight ratio is from 150:1 to 1:1.

10. The composition of claim 9 which is a microsuspension of D-AHII wherein the D-AHII:surfactant weight ratio is from 150:1 to 20:1.

11. The composition of claim 9 which is a nanosuspension of D-AHII wherein the D-AHII:surfactant weight ratio is from 7.5:1 to 5:1.

12. The composition of claim 1 further comprising a viscosity modifying agent which is PEG 3350 or sodium carboxymethylcellulose or a combination of both, wherein the concentration of the viscosity modifying agent is from 0.1 wt % to 3.0 wt % and the viscosity of the suspending vehicle is from 1.4 cP to 1220 cP.

13. The composition of claim 1 wherein the pH of the composition is 7.

14. The composition of claim 13 comprising a phosphate buffering agent.

15. The composition of claim 1 further comprising a tonicity modifier which is one or more of dextrose, mannitol, sucrose, trehalose or sodium chloride.

16. The composition of claim 15 wherein the tonicity modifier is:
(a) for a microsuspension, mannitol or sodium chloride or a combination of both; or
(b) for a nanosuspension, one or more of sucrose, trehalose or sodium chloride.

17. The composition of claim 16 wherein the tonicity modifier is:
(a) for a microsuspension, sodium chloride; or
(b) for a nanosuspension, trehalose.

18. The composition of claim 1 comprising:

| Components | Quantity |
| --- | --- |
| D-AHII | 30.0% (w/v) |
| Polyethylene glycol 3350 | 3% (w/v) |
| Polysorbate 80 | 0.2% (w/v) |
| Phosphate buffer | 10 mM |
| Water | QS to 100% |
| pH | 7.0 |
| Particle size distribution, micron ($D_{10}/D_{50}/D_{90}$) | 2.58/7.61/15.33 |
| Specific surface area (m²/g) | 1.82. |

* * * * *